(12) United States Patent
Huai et al.

(10) Patent No.: US 11,202,558 B1
(45) Date of Patent: Dec. 21, 2021

(54) INTERACTIVE MAGNETICALLY CONTROLLED CAPSULE ENDOSCOPE AUTOMATIC CRUISE EXAMINATION SYSTEM

(71) Applicant: Xiaoming Huai, Snnyvale, CA (US)

(72) Inventors: Xiaoning Huai, Sunnyvale, CA (US); LiangXin Wu, Shenzhen (CN); ShuXian Kan, Shenzhen (CN); Gang Bi, Shenzhen (CN)

(73) Assignee: Shenzhen Jifu Medical Technology Co., LTD, Shenzhen (CN)

( * ) Notice: Subject to any disclaimer, the term of this patent is extended or adjusted under 35 U.S.C. 154(b) by 0 days.

(21) Appl. No.: 17/317,966

(22) Filed: May 12, 2021

(51) Int. Cl.
*A61B 1/04* (2006.01)
*A61B 5/11* (2006.01)
*A61B 1/00* (2006.01)

(52) U.S. Cl.
CPC .......... *A61B 1/041* (2013.01); *A61B 1/00158* (2013.01); *A61B 5/1116* (2013.01); *A61B 1/00016* (2013.01)

(58) Field of Classification Search
CPC . A61B 1/00016; A61B 1/00158; A61B 1/041; A61B 5/1116
See application file for complete search history.

(56) References Cited

U.S. PATENT DOCUMENTS

| | | | | |
|---|---|---|---|---|
| 2005/0124875 A1* | 6/2005 | Kawano | ............... | A61B 5/4839 600/407 |
| 2006/0052667 A1* | 3/2006 | Palti | ................... | A61B 5/14539 600/160 |
| 2008/0177177 A1* | 7/2008 | Aoki | ...................... | A61B 5/062 600/424 |
| 2009/0292174 A1* | 11/2009 | Shigemori | ............. | A61B 5/062 600/117 |
| 2011/0237889 A1* | 9/2011 | Tanaka | ............... | A61B 1/00039 600/118 |
| 2011/0245731 A1* | 10/2011 | Chiba | .................... | A61B 5/062 600/587 |
| 2013/0038711 A1* | 2/2013 | Sato | ..................... | A61B 1/0005 348/68 |
| 2014/0378762 A1* | 12/2014 | Hirabayashi | ....... | A61B 1/00156 600/109 |
| 2016/0166133 A1* | 6/2016 | Chiba | ................... | A61B 5/1116 600/109 |

\* cited by examiner

*Primary Examiner* — Aaron B Fairchild

(57) ABSTRACT

An interactive magnetically controlled capsule endoscopy system comprises a pose monitoring module, an automatic cruise control module, a capsule and a human-computer interaction module. The pose monitoring module is configured to continuously detect pose of a subject in real time, and the automatic cruise control module includes a magnetron device and a control terminal, wherein the magnetron device is configured to generate a driving magnetic field to drive the capsule to move in the digestive tract of the subject and the control terminal runs an automatic cruise examination program. The automatic cruise examination program is configured to initiate a pose change whenever needed by the automatic cruise examination program, perform real-time alignment of the magnetron device, so that the subject is within the effective working range of the driving magnetic field and drive the capsule to move in and acquire image data of the digestive tract of the subject according to data of the pose of the subject.

1 Claim, 3 Drawing Sheets

INTERACTIVE MAGNETICALLY CONTROLLED CAPSULE ENDOSCOPE AUTOMATIC CRUISE EXAMINATION SYSTEM

TECHNICAL FIELD

The present invention relates to the technical field of medical devices, in particular to a capsule endoscope.

BACKGROUND

A capsule endoscope with a built-in magnet moves in the digestive tract of a subject under the drive of a magnetic field generated by a magnetron device. The camera built in the capsule takes pictures of various parts of the digestive tract of a subject, and the captured image signal is sent to the control processing terminal of the system by a built-in wireless transceiver. The control terminal further processes the image for a doctor to make a diagnosis. The prior art magnetron capsule endoscope requires an operator to monitor according to personal clinical experience while controlling the movement of the capsule in the digestive tract of the subject through the magnetron device. Substituting an automatic cruise examination program for the manual operation can not only reduce the labor intensity of the staff, but also reduce errors in diagnosis miss and improve the examination efficiency.

SUMMARY OF THE INVENTION

The invention discloses an interactive magnetically controlled capsule endoscopy examination platform, which includes a camera continuous monitoring the subject's pose and acquiring data of the subject's pose. The automatic cruise examination program interacts with the subject through a human-computer interaction device, initiating changing the pose of the subject on a per needed basis in a timely manner, adjusting the examination process according to the pose and expressed demands of the subject, and completing the examination accurately and quickly.

Figure 1:
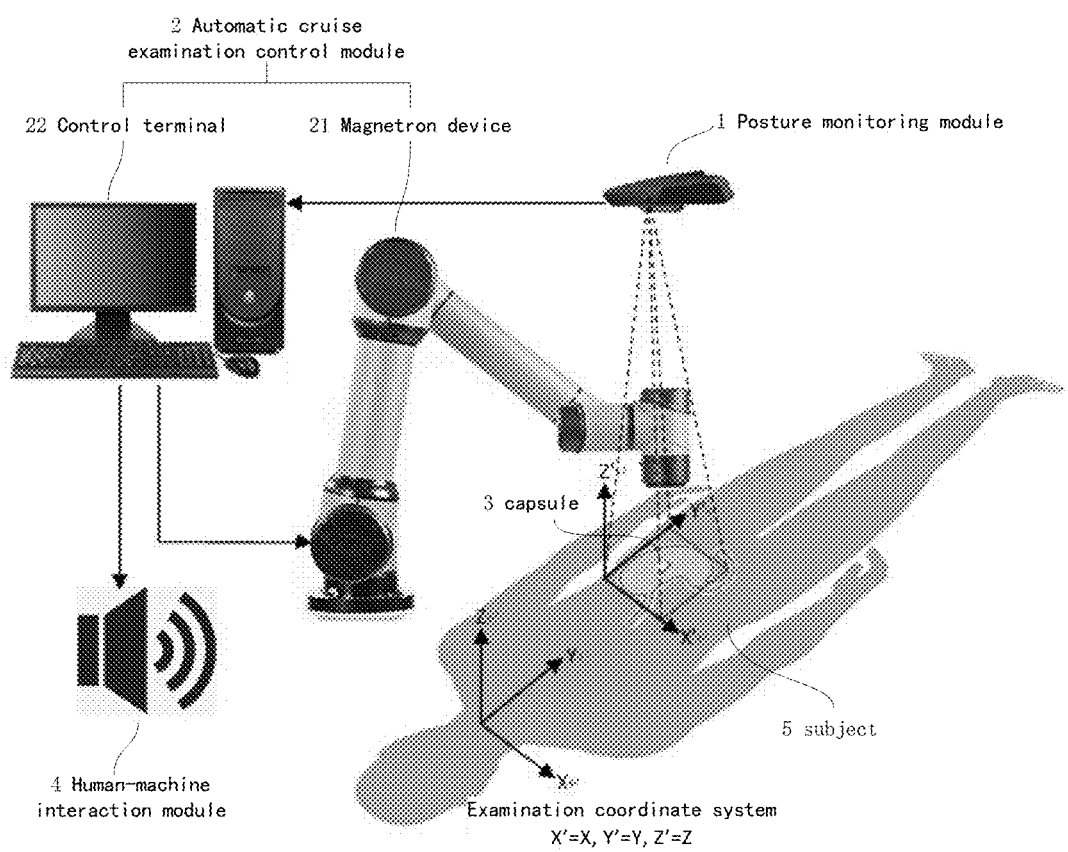

As shown in FIG. 1, the interactive magnetically controlled capsule endoscopy system includes: a pose monitoring module 1, an automatic cruise control module 2, a capsule module 3 hereinafter referred to as capsule and a human-computer interaction module 4; The pose monitoring module 1, the automatic cruise control module 2, the capsule 3 and the human-computer interaction module 4 are connected by a communication link; The pose monitoring module 1 is conFIG.d to continuously detect the pose of the subject in real time, and obtain at least one set of data of the pose of the subject 5. The capsule 3 is conFIG.d to acquire image data of the digestive tract of the subject 5; The human-computer interaction module 4 is conFIG.d to initiate the subject to change the pose and obtain the subject's demands through the human-machine interface 4; The automatic cruise control module 2 includes: a magnetron device 21 and a control terminal 22; the magnetron device 21 is conFIG.d to generate a magnetic field that drives the capsule to move in the digestive tract of the subject; the control terminal 22 runs an automatic cruise examination program; the automatic cruise examination program is conFIG.d to: initiate the subject to change the position and pose at the right time, determine the pose of the subject according to the at least one set of data, determine the position and pose of the capsule under the pose of the subject 3, and drive the capsule 3 to move in the digestive tract of the subject; Acquire image data; align the magnetron device in real time, so that the subject is within the effective working range of the driving magnetic field; Adjust the examination process with reference to the subject's pose and demands, including suspending the examination when the subject leaves an examination position without authorization, or the pose does not meet the requirements of examination procedures, or when it is requested by the subject to stop the examination. The automatic cruise examination program is further conFIG.d to: generate a relative movement between the capsule and a stomach wall of the subject by changing the pose of the subject, and expand shooting angles and acquire multiple images of a spot through the relative movement; increase frame rates of images taken by the capsule during a change of the pose of the subject.

BRIEF DISCUSSION OF THE DRAWINGS

Figure 2:
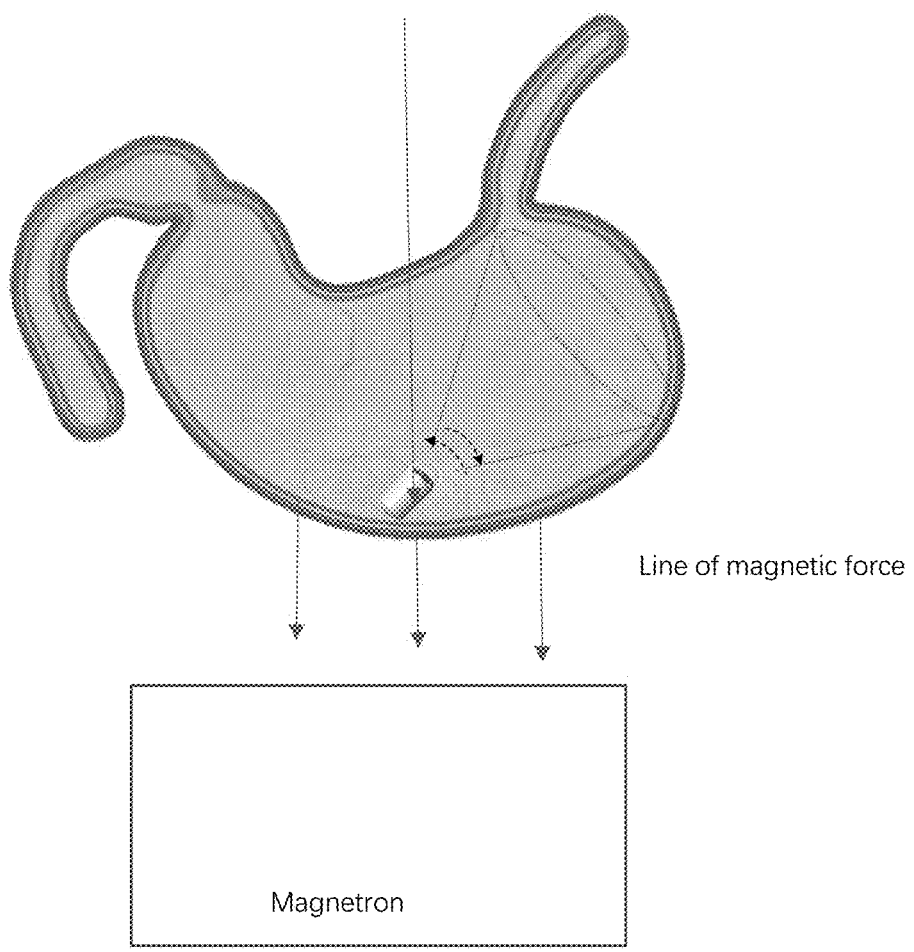
Figure 3:
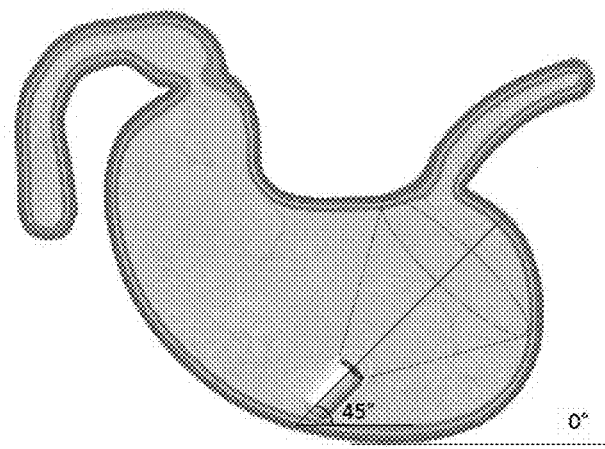
Figure 3:
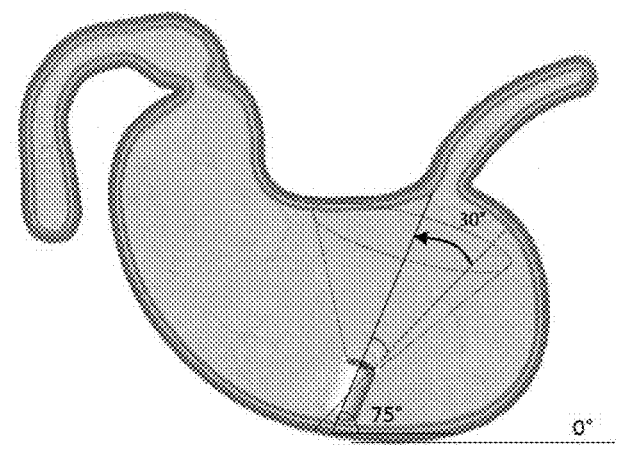
Figure 3:
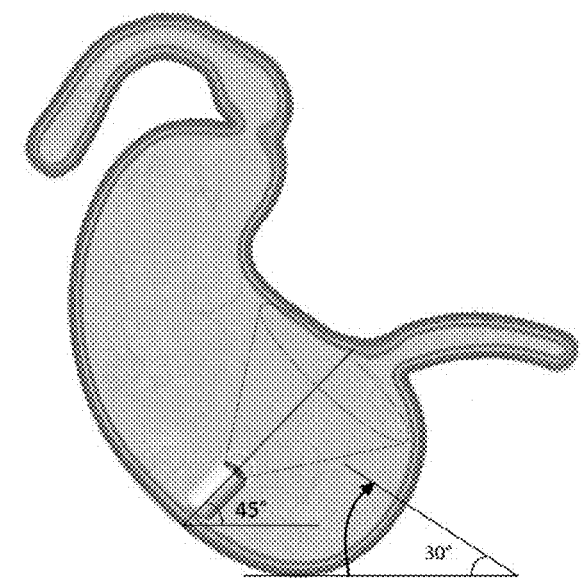

FIG. 1 The system composition.
FIG. 2 An illustration of "Capsule is stuck on the gastric wall".
FIG. 3 An illustration of the relative movement between the capsule and the gastric wall generated by pose change of a subject.

DETAILED DESCRIPTION

The interactive magnetically controlled capsule endoscopy system is shown in FIG. 1. After the subject swallows the capsule, the interactive magnetically controlled capsule endoscopy system starts the automatic cruise examination program. The interactive magnetron capsule endoscopy system includes a pose monitoring module 1, an automatic cruise control module 2, a capsule 3, and a human-computer interaction module 4, The pose monitoring module 1, automatic cruise control module 2, capsule 3 and human-computer interaction module 4 are connected through a communication link, as shown in FIG. 1. The automatic cruise control module 2 includes: a magnetron device 21, a control terminal 22, a mechanical device for rotating an examination bed; capsule 3 includes: an image sensor, a permanent magnet, a wireless transceiver. The pose monitoring module 1 includes: one or more cameras and a pose detection and extraction module to obtain data of the position and posture of the subject 5 in an examination platform coordinate system. The examination platform coordinate system may be any three-dimensional space coordinate system, including a preferred x, y, z rectangular coordinate system with sea level as the x, y plane and z coordinate axis in the vertical direction. Further, the examination platform coordinate system may include an examination bed on which the subject is lying as an x, y plane, and the vertical upward direction as z coordinate axis. In a preferred embodiment, the pose of the subject may include a standing posture, a supine posture, and a lateral posture. The human body is a non-rigid body, and the standing posture preferably involves the subject naturally standing on the x, y plane of the examination platform coordinate system, being able to rotate any angle around the z coordinate axis. The supine posture relates preferably the subject lying naturally on an examination bed, the bearing plane of the examination bed is the x, y plane of the examination platform coordinate system, and the subject or the examination bed carrying the subject can rotate any angle within the x, y plane of the examination platform coordinates system around the z coordinate axis. The lateral posture preferably refers to the subject lying laterally on the examination bed naturally, and the subject or the examination table carrying the subject can rotate any angle around the z coordinate axis. The lateral posture includes a left lateral posture and a right lateral posture, corresponding to the left and right sides of the subject. The pose monitoring module 1 provided by the present invention can not only obtain the accurate data of the above-mentioned posture, but also obtain minor movement of the subject when lying supine, that is, data of small changes in pose. The pose of the capsule 3 refers to the coordinates of the capsule position and angle in the same examination platform coordinate system, as shown in FIG. 1.

The human-computer interaction module 4 interacts with the subject through the human-machine interface to initiate the subject to change pose and receive the demands of the subject expressed. The human-machine interface includes, but is not limited to, acoustic, visual and tactile medium.

The control terminal of the automatic cruise control module 2 runs the automatic cruise examination program. The magnetron device 21 drives the capsule 3 to move directionally in the digestive tract of the subject 5. The image sensor of the capsule acquires images of the digestive tract and sends the images to the automatic cruise control module 2 through the wireless transceiver. The control terminal 22 performs feature analysis and quality evaluation on the images to ensure the completeness and effectiveness of the examination. The automatic cruise examination program is preferably used for gastric examination. The subject needs to drink a lot of water before the examination. The density of the capsule can be equal to or greater than the density of the water. The movement of the capsule in the stomach is preferably carried out in water. The magnetic fields generated by the magnetron device 21 preferably includes a positioning magnetic field and a driving magnetic field. The capsule is stuck to the side of the stomach wall close to the magnetron device under the positioning magnetic field, which constructs a characteristic scenario of "capsule is stuck to the stomach wall.", as shown in FIG. 2. The driving magnetic field of the magnetron device 21 drives the capsule to translate or rotate in the digestive tract and sequentially capture image data of each characteristic point of the stomach until it is confirmed that the image acquisition of all parts of the stomach is completed. For this purpose, the automatic cruise examination program needs to determine current and historical values of the position and of the pose of main axis of the capsule, that is, the image shooting direction; find out and drive the capsule to the next future position and posture. Due to "capsule is stuck to the stomach wall", the movement between the capsule and the stomach wall is relative, wherein a rotation of an angle of a by the stomach caused by a change of the pose of the subject may correspond to a rotation of an angle of −α by the main axis of the capsule, as shown in FIG. 3.

In one embodiment, the automatic cruise examination program may preferably use a combination of standing posture, supine posture, and lateral posture to complete an examination. During an examination in one of the postures, the automatic cruise examination program may preferably prompt the subject to make appropriate small-range pose adjustments, and use the pose adjustments to improve the performance of the examination, including: Due to the magnetic control of the capsule is not accurate in general, there are occasions that the capsule is stuck and cannot see the full picture of a feature spot, the relative movement between the stomach wall and the capsule generated by changing the subject's posture may help expand the field of view of the capsule and allow the capsule to capture the full picture of the feature spot, which may further preferably improve the accuracy of identifying the location of the feature spot resulting in improved positioning of the capsule. Furthermore, the moving of capsule may be obstructed by tissue structures of the digestive tract surface, causing the actual position and pose of the capsule to deviate from the path set by the automatic cruise examination program. Changing the subject's pose may preferably generate changes in the relative position of the inner wall of the digestive tract and the capsule, thus helping the capsule to overcome or bypass the obstacle.

In another embodiment, the automatic cruise examination program continuously monitors the pose data of the subject after initiating a pose change, and when it is determined that the subject is in the pose change, appropriately increase the image capture frame rate of the capsule to obtain continuous images of the stomach.

In another embodiment, after the capsule enters the digestive tract of the subject, the automatic cruise examination program automatically completes the preset examination without the intervene by the medical staff.

In another embodiment, the automatic cruise examination program can accept request input by the subject entered though a human-machine interface and adjust the examination process according to the request of the subject, including suspending the examination process when the subject actively requests it.

In another embodiment, the interactive magnetically controlled capsule endoscopy system can reduce the psychological pressure and nervousness of the subject during the examination and obtain a relaxed and pleasant user experience.

What is claimed is:

1. An interactive magnetically controlled capsule endoscopy system, comprising:
  a pose monitoring module, an automatic cruise control module, a capsule and a human-computer interaction module;
  the pose monitoring module, the automatic cruise control module, the capsule, and the human-computer interaction module configured to be connected by a communication link;
  the pose monitoring module configured to use a video camera to continuously obtain data of pose of a subject;
  the capsule configured to acquire image data of a digestive tract of the subject;
  the human-computer interaction module configured to initiate the subject to change pose through a human-machine interface including one or more modalities of acoustic, visual and tactile medium;
  the automatic cruise control module comprises a magnetron device and a control terminal;
  the magnetron device configured to generate a driving magnetic field to drive the capsule to move in the digestive tract of the subject;
  the control terminal configured to run an automatic cruise examination program;
  the automatic cruise examination program configured to send control signals to:
    cause the human-computer interaction module to initiate the subject to change pose as required;
    cause the human-computer interaction module to initiate the subject to change pose such that a relative movement is generated between the capsule and a stomach wall of the subject, cause the capsule to expand shooting angles and acquire multiple images of a spot during the relative movement, and cause the magnetron equipment to perform alignment, so that the subject is within an effective working range of the driving magnetic field.

\* \* \* \* \*